(12) United States Patent
Wang et al.

(10) Patent No.: US 6,545,057 B2
(45) Date of Patent: Apr. 8, 2003

(54) TRICYCLIC ANTIDEPRESSANTS AND THEIR ANALOGUES AS LONG-ACTING LOCAL ANESTHETICS AND ANALGESICS

(75) Inventors: Ging Kuo Wang, Westwood, MA (US); Peter Gerner, Weston, MA (US)

(73) Assignee: The Brigham and Women's Hospital Inc., Boston, MA (US)

( * ) Notice: Subject to any disclaimer, the term of this patent is extended or adjusted under 35 U.S.C. 154(b) by 0 days.

(21) Appl. No.: 09/965,138

(22) Filed: Sep. 26, 2001

(65) Prior Publication Data

US 2002/0094975 A1 Jul. 18, 2002

Related U.S. Application Data

(60) Provisional application No. 60/235,432, filed on Sep. 26, 2000.

(51) Int. Cl.[7] ............................................. A61K 31/135
(52) U.S. Cl. ................... 514/656; 514/211.089; 514/211.13; 514/217; 514/254.06; 514/459; 514/649; 514/653
(58) Field of Search .................. 514/211.13, 211.08, 514/217, 254.06, 450, 649, 653, 656

(56) References Cited

U.S. PATENT DOCUMENTS

| | | | |
|---|---|---|---|
| 2,554,736 A | | 5/1951 | Haefliger et al. |
| 3,576,853 A | | 4/1971 | Kaiser et al. |
| 3,998,810 A | | 12/1976 | Wiedemann et al. |
| 5,860,950 A | * | 1/1999 | Demopulos et al. ........... 604/49 |
| 6,211,171 B1 | * | 4/2001 | Sawynok et al. ...... 514/211.13 |
| 2001/0036943 A1 | * | 11/2001 | Coe et al. ................... 514/220 |

FOREIGN PATENT DOCUMENTS

| | | |
|---|---|---|
| CH | 534124 A | 2/1973 |
| WO | WO 95/17903 A1 | 7/1995 |
| WO | WO 95/18186 A1 | 7/1995 |
| WO | WO 99/59598 A1 | 11/1999 |
| WO | WO 02/060870 A2 | 8/2002 |

OTHER PUBLICATIONS

Elden, et al., "Zur Analyse von Psychopharmaka: Lofepramin (Gamonil ®)" *Pharmazaulische Zeitung* 123 (1978) 1796–1801 and English language abstract.

Fomenko, et al., "Chemical heterogeneity of [$^3$H]imipramine binding sites on human platelet membranes" *European Journal of Pharmacol.–Molecular Pharmacology Section* 189 (1990) 175–183.

Li, et al., "Hexamethonium–Type Allosteric Modulators of the Muscarinic Receptors Bearing Lateral Dibenzazepine Moieties," *Arch. Pharm. Pharm. Med. Chem.* 334, (2001) 121–124.

Enlund, A. M., et al., "Capillary electrochromatography of tricyclic antidepressants on strong cation exchangers with different pore sizes," *Journal of Chromatography* A 918 (2001) 211–220.

Maxwell, R.A., et al., "Molecular Features Affecting The Potency of Tricyclic Antidepressants and Structurally Related Compounds as Inhibitors of The Uptake of Tritiated Norepinephrine by Rabbit Aortic Strips", *The Journal of Pharmacology and Experimental Therapeutics*, 166 (2) (1969) 320–329.

Abdi et al. "The anti–allodynic effects of amitriptyline, gabapentin, and lidocaine in a rat model of neuropathic pain," *Anesth Analg* Dec. 1998;87:1360–6.

Barber et al., "Blockade of Cardiac Sodium Channels by Amitriptyline and Diphenylhydantoin" *Circulation Research* vol. 69, No. 3 Sep. 1991:677–696.

Cerda et al., "A Physiologic Assessment of Intrathecal Amitriptyline in Sheep." *Anesthesiology*, May 1997; 86(5): 1094–1103.

Esser et al., "Acute amitriptyline in a rat model of neuropathic pain: differential symptom and route effects," *Pain* 80 (1999) 643–653.

Esser et al., "Local Peripheral Action of Antidepressants in Rat Models of Neuropathic Pain And Inflammation," Presented Nov. 26, 1998, Supported by the Medical Research Council of Canada.

Heughan et al., "Peripheral Amitriptyline Suppresses Formalin–Induced Fos Expression in the Rat Spinal Cord," *Anesth Analg*, 2002, 94: 427–431.

Max et al., "Effects of desipramine, amitriptyline, and fluoxetine on pain in diabetic neuropathy," *New England J Med* 326:1250–6, 1992.

Pancrazio et al., "Inhibition of Neuronal Na$^+$ Channels by Antidepressant Drugs" *The Journal of Pharmacology and Experimental Therapeutics*, 1998, 284; 208–214.

* cited by examiner

Primary Examiner—James H. Reamer
(74) *Attorney, Agent, or Firm*—Wolf, Greenfield & Sacks PC

(57) ABSTRACT

Methods and compositions of tricyclic antidepressants for inducing local long-lasting anesthesia and analgesia are provided. The methods and compositions are useful for alleviating acute and chronic pain, particularly useful for treating a localized pain.

16 Claims, 11 Drawing Sheets

TRICYCLIC ANTIDEPRESSANTS AND THEIR ANALOGUES AS LONG-ACTING LOCAL ANESTHETICS AND ANALGESICS

RELATED APPLICATIONS

This application claims priority under 35 U.S.C. §119 to U.S. provisional application Ser. No. 60/235,432, filed Sep. 26, 2000.

GOVERNMENT SUPPORT

This work was funded in part by grant numbers GM48090 from the National Institutes of Health. Accordingly, the government may have certain rights to this invention.

FIELD OF THE INVENTION

This invention relates to the use of the tricyclic antidepressants to produce local long-acting relief of different varieties of pain.

BACKGROUND OF THE INVENTION

To provide a better understanding of the invention it is necessary to distinguish between the two terms analgesia and anesthesia. Analgesia is defined as a condition in which nociceptive stimuli are sensed but are not interpreted as pain. Anesthesia is a state characterized by total loss of sensation, the result of pharmacologic depression of nerve function. Thus, analgesia does not produce anesthesia whereas anesthesia produces analgesia.

In general, pain is associated with a known tissue pathology (e.g., cancer pain, arthritic pain), inflammation, or injury to a body tissue (e.g., surgery). Neuropathic pain is thought to be a consequence of damage to peripheral nerves or to regions of the central nervous system. Neuropathic pain can present as an acute pain but frequently occurs as a form of chronic pain.

The use of long-acting local anesthetics that elicit complete neural blockage for more than several hours is frequently desirable in the management of acute and chronic pain. Pain relief research during the last two decades has focused on the identification of new local anesthetics to produce analgesia of long duration with minimal impairment of autonomic function and low toxicity. One of the best known "long-acting" local anesthetics developed to date, bupivacaine, reportedly blocks major nerve block for three to twelve hours. Unfortunately, bupivacaine is also highly cardiotoxic. The development of alternative "long-acting" local anesthetics met limited success.

Pain relief research also has focussed on the identification of new neurolytic agents for the treatment of chronic pain and intractable cancer pain. Historically, spinal opiate administration, surgical intervention, or both have been used to alleviate chronic and intractable cancer pain. When these methods fail to provide insufficient pain relief, phenol or absolute alcohol reportedly have been used as neurolytic agents to destroy the pathogenic nerve regions that are responsible for pain manifestation. However, these agents exert only weak local anesthetic effects and, accordingly, have been difficult to administer to alert patients without inducing additional pain. To date, a long-acting local anesthetic with no major side effects has not been available for the treatment of acute and chronic pain.

In view of the foregoing limitations of the existing local anesthetics to prolong the duration of anesthesia, a need still exists for useful long-acting local anesthetics for pain management. Preferably such local long-acting anesthetics also will exhibit reversible effects. Such drugs would be useful and desirable, for example, in postoperative analgesia, and for treating acute and chronic pain. Preferably, such agents would have sufficient potency to permit administration of a single, relatively low dosage of the agent, thereby minimizing the likelihood of side effects that have been attributed to the existing local long-acting anesthetic agents.

Tricyclic antidepressants are frequently used as analgesics in pain management but only when administered systemically. Among them, amitriptyline has been used orally for the analgesic therapy of chronic pain. Amitriptyline's sites of action are both central and peripheral. Despite the numerous reports on amitriptyline's analgesic effect on reducing pain when administered systemically, the exact mechanism of this effect remains unknown. To our knowledge, tricyclic antidepressants have not been used as local analgesics. Likewise, they have not been used at all as anesthetics either locally or systemically.

SUMMARY OF THE INVENTION

The invention involves in one respect the surprising discovery that tricyclic antidepressants act as long-acting local anesthetics and analgesics that are useful for alleviating pain. These tricyclic antidepressants exhibit unexpected anesthetic and analgesic properties compared to related compounds that previously have been used for pain management. The availability of compounds with strong local long-acting anesthetic properties, such as that of tricyclic antidepressants described herein, are advantageous over the existing compounds for pain management because conventional neurolytic agents typically exert only weak local anesthetic effects which are of short duration and produce irreversible damage to the nerves.

According to one aspect of the invention, a method for inducing local anesthesia in a subject is provided. The method involves administering locally to a subject in need of such a treatment an effective amount of a tricyclic antidepressant in an amount effective to block sensory and motor functions of a nerve(s) at the site of administration of the tricyclic antidepressant. The tricyclic antidepressant is selected from those described in the formulas below.

In one embodiment, the tricyclic antidepressant is amitriptyline or one of its analogues. Analogues of amytripyline include quaternary and tertiary analogues. Examples of quaternary amytripyline analogues include but are not limited to N-phenyl-propyl amitriptyline bromide, N-phenyl-ethyl amitriptyline bromide, or N-phenyl-methyl amitriptyline bromide. Tertiary amitriptyline analogues include but are not limited to N-phenyl-propyl nortriptyline bromide, N-phenyl-ethyl nortriptyline bromide, or N-phenyl-methyl nortriptyline bromide. A preferred quaternary analogue is N-phenyl-ethyl amitriptyline bromide.

The tricyclic antidepressant is administered in a therapeutically effective amount sufficient to induce anesthesia in a subject at the site of administration for at least 30 minutes, 60 minutes, 2 hours, 4 hours, 8 hours, 12 hours, 24 hours, 48 hours, 72 hours, or 96 hours.

The compounds of the invention are useful when administered locally in treating all categories of pain, whether acute or chronic, local or general. The subject according to the invention can be experiencing or at risk of experiencing any of the forgoing categories of pain. Examples of different kinds of pain are described in the Detailed Description.

The compounds of the invention can be administered to sites well known by those of ordinary skill in the art to be appropriate for interfering with the nerve(s) propagating such pain.

In one embodiment of the invention, the tricyclic antidepressant is administered in the lower back to alleviate pain. In another embodiment, the tricyclic antidepressant is administered to alleviate pain propagated by the sciatic nerve.

The preferred mode of administration is local administration such as by injection, intramuscularly, subcutaneously, dermally, or intradermally by inhalation or by local application topically such as in a lotion or a patch.

In yet another aspect of the invention, a method for inducing local analgesia in a subject is provided. The method involves administering locally to a subject in need of such a treatment an effective amount of a tricyclic antidepressant in an amount effective to block sensory function of a nerve(s) at the site of administration of the tricyclic antidepressant. The tricyclic antidepressant is selected from those described in the formulas below.

In one embodiment, the tricyclic antidepressant is amitriptyline or one of its analogues. Analogues of amytripyline are quaternary and tertiary analogues. Examples of quaternary amytripyline analogues include but are not limited to N-phenyl-propyl amitriptyline bromide, N-phenyl-ethyl amitriptyline bromide, or N-phenyl-methyl amitriptyline bromide. Tertiary amitriptyline analogues include but are not limited to N-phenyl-propyl nortriptyline bromide, N-phenyl-ethyl nortriptyline bromide, or N-phenyl-methyl nortriptyline bromide. A preferred analogue is N-phenyl-ethyl amitriptyline bromide.

The tricyclic antidepressant is administered in a therapeutically effective amount sufficient to induce analgesia in a subject at the site of administration for at least 30 minutes, 60 minutes, 2 hours, 4 hours, 8 hours, 12 hours, 24 hours, 48 hours, 72 hours, or 96 hours.

The compounds of the invention are useful when administered locally in treating all categories of pain, whether acute or chronic, local or general. The subject according to the invention can be experiencing or at risk of experiencing any of the forgoing categories of pain. Examples of the different kinds of pain are described in the Detailed Description.

The compounds of the invention can be administered to sites well known by those of ordinary skill in the art to be appropriate for interfering with the nerve(s) propagating such pain.

In one embodiment of the invention, the tricyclic antidepressant is administered in the lower back to alleviate pain. In another embodiment, the tricyclic antidepressant is administered to alleviate pain propagated by the sciatic nerve.

The preferred mode of administration is local administration such as by injection, intramuscularly, subcutaneously, dermally, or intradermally, by inhalation or by local application topically such as in a lotion or a patch.

In some embodiments the tricyclic antidepressants are: amytriptyline, amoxapine, clomipramine, desipramine, doxepin, imipramine, nortriptyline, protriptyline, trimipramine, or one of their analogues including quaternary and tertiary.

In some embodiments, the tricyclic antidepressant is an analogue of any number of well-known trycyclic antidepressants modified at the nitrogen which forms part of the carbon chain attached to the tricyclic moiety. Preferred are amphipathic derivatives of tricyclic antidepressants. In important embodiments, the derivatives are quaternary analogues. In other embodiments, the derivatives are tertiary analogues.

It is preferred that the analogues of the tricyclic antidepressants be such that the hydrophobicity of the tricyclic antidepressant is increased. It is also preferred that the hydrophobicity-increasing moiety be a moiety which would not insert within and be captured by a lipid membrane (e.g., moieties that are long, unbranched alkyls such as $C_6$ or greater chains).

Preferred quaternary or tertiary amine derivatives of the tricyclic antidepressants are cyclic derivatives such as, a phenyl-methyl, phenyl-ethyl, phenyl-propyl, or phenyl-butyl derivative. The preferred compound is:

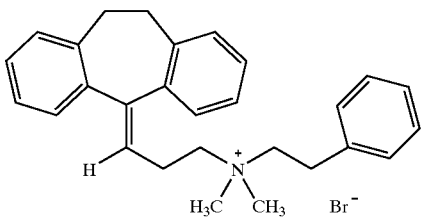

Other important tricyclic antidepressants which can be derivatized as described above include:

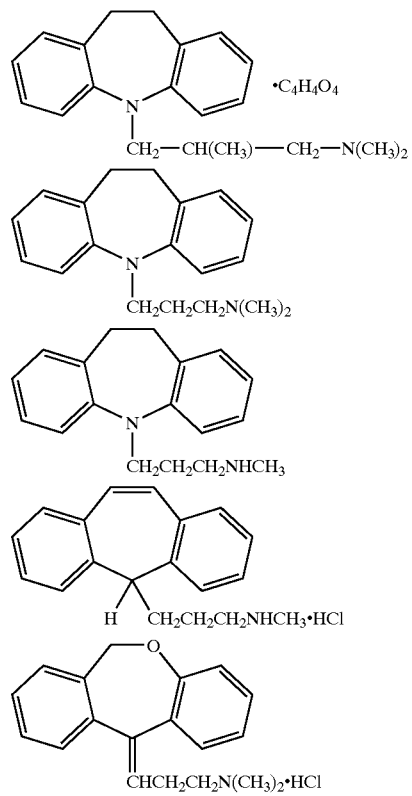

An important subclass of the tricyclic antidepressants can be represented by the following formula:

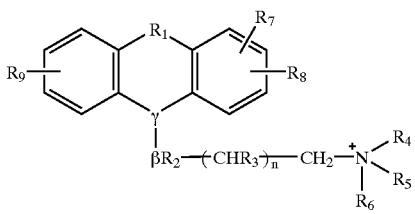

wherein $R_1$ equals C—C, C—O or C=C

γ-β equals C=C, N—C or CH—C n equals 1, 2, 3, 4, 5, or 6

$R_2$ equals H or $H_2$ $R_3$ equals H or $CH_3$ or nothing $R_4$ equals H or $R_6$ $R_5$ equals H or $R_6$ $R_6$ equals ($C_1$-$C_8$) alkyl, ($C_1$-$C_8$) substituted alkyl, ($C_1$-$C_8$) alkenyl, ($C_1$-$C_8$) substituted alkenyl, ($C_1$-$C_8$) alkynyl, ($C_1$-$C_8$) substituted alkynyl (wherein the substituents can be ($C_1$-$C_4$) alkyl, ($C_1$-$C_4$) substituted alkyl, ($C_1$-$C_4$) alkenyl, ($C_1$-$C_4$) substituted alkenyl, ($C_1$-$C_4$) alkynyl, ($C_1$-$C_4$) substituted alkynyl), or $R_6$ is nothing, $R_7$ equals H or Cl $R_8$ equals H or Cl $R_9$ equals H or Cl, and wherein when $R_1$ equals C=C, at least one of $R_4$, $R_5$, and $R_6$ is 2, 3, 4, 5, 6, 7, 8, 9, 10, 11, or 12 carbons in length.

In one important embodiment, when $R_1$ equals C—C, γ-β equals C=C, and n equals 1, at least one of $R_4$, $R_5$, and $R_6$ is not $CH_3$ (when $R_6$ is present) and at least one of $R_4$ and $R_5$ is not $CH_3$ (when $R_6$ is not present).

In one important embodiment $R_1$ equals C—C. In another important embodiment $R_1$ equals C—O. In another important embodiment $R_1$ equals C=C. In another important embodiment γ-β equals N—C. In another important embodiment n equals 1. In still another important embodiment n equals 2. In yet another important embodiment, at least one of $R_4$, $R_5$, and $R_6$ contains 2, 3, 4, 5, 6, 7, 8, 9, 10, 11 or 12 carbons. Important compounds of this embodiment have at least one of $R_4$, $R_5$, and $R_6$ containing 4, 5, 6, 7, 8, 9, 10, 11 or 12 carbons. Other important compounds of this embodiment have at least one of $R_4$, $R_5$, and $R_6$ containing 6, 7, 8, 9, 10, 11 or 12 carbons. Still other important compounds of this embodiment include quaternary and tertiary amine derivatives. Other important compounds of this embodiment have $R_1$ equals C—C. In still other important embodiments, $R_7$, $R_8$, and $R_9$ are H.

According to another aspect of the invention, compositions of matter are provided. The compositions of matter are quaternary amine derivatives of tricyclic antidepressants, such as those described above. Preferred derivatives are those described above.

The invention also involves pharmaceutical preparations comprising:

an effective amount of any one of the foregoing compositions of matter, and a pharmaceutically-acceptable carrier.

The invention further involves pharmaceutical preparations comprising:

a tricyclic antidepressant or analogue thereof, an anti-inflammatory agent, and a pharmaceutically-acceptable carrier.

The invention also involves pharmaceutical preparations comprising:

a tricyclic antidepressant or analogue thereof in a topical formulation or aerosol formulation, such as a cream, lotion, ointment, propellant, patch, and the like.

These and other aspects of the invention will be described in greater detail below.

These and other aspects of the invention, as well as various advantages and utilities will be more apparent with reference to the drawings and the detailed description of the preferred embodiments.

All references, patents, and patent publications identified in this document are incorporated in their entirety herein by reference.

DETAILED DESCRIPTION OF THE INVENTION

Figure 1A:
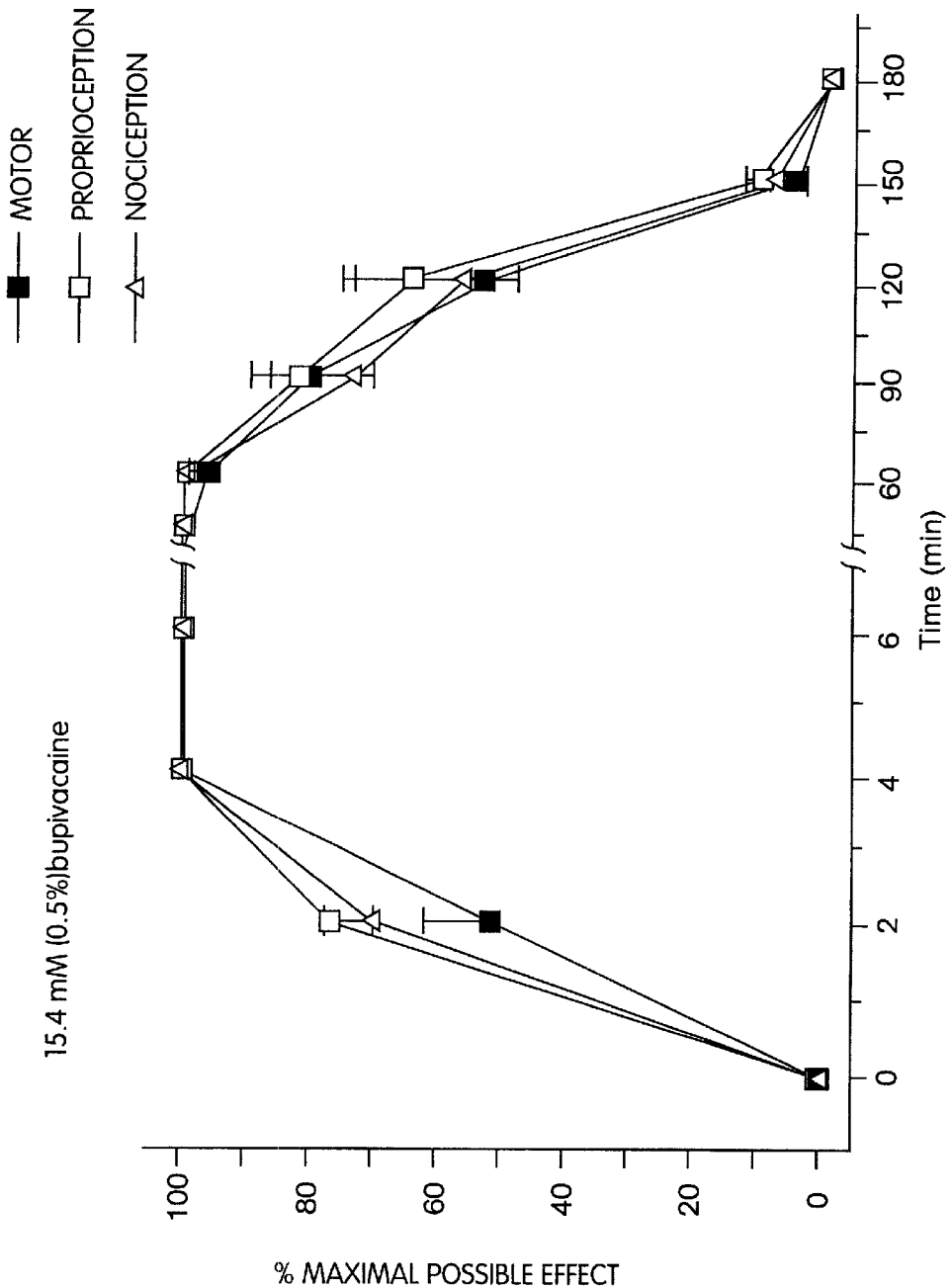
FIG. 1. Graph showing the time course of propioceptive, motor, and nociceptive functional impairment after sciatic nerve block with (A) 15.4 mM bupivacaine, (B) 5 mM amitriptyline, or (C) 10 mM amitriptyline expressed as percent maximal possible effect (% MPE). Percent maximal possible effect (% MPE) is plotted against time.
Figure 1B:
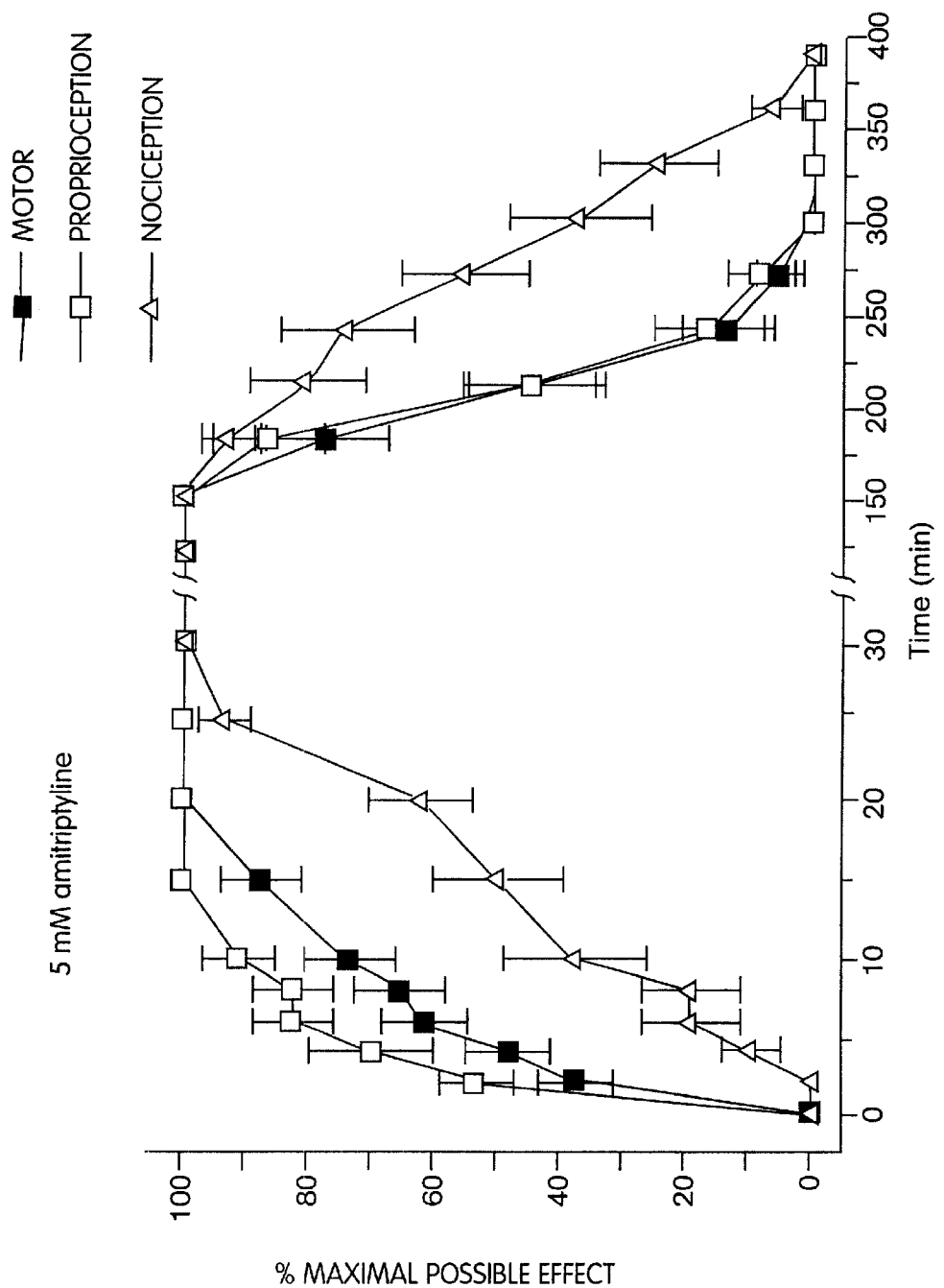
Figure 1C:
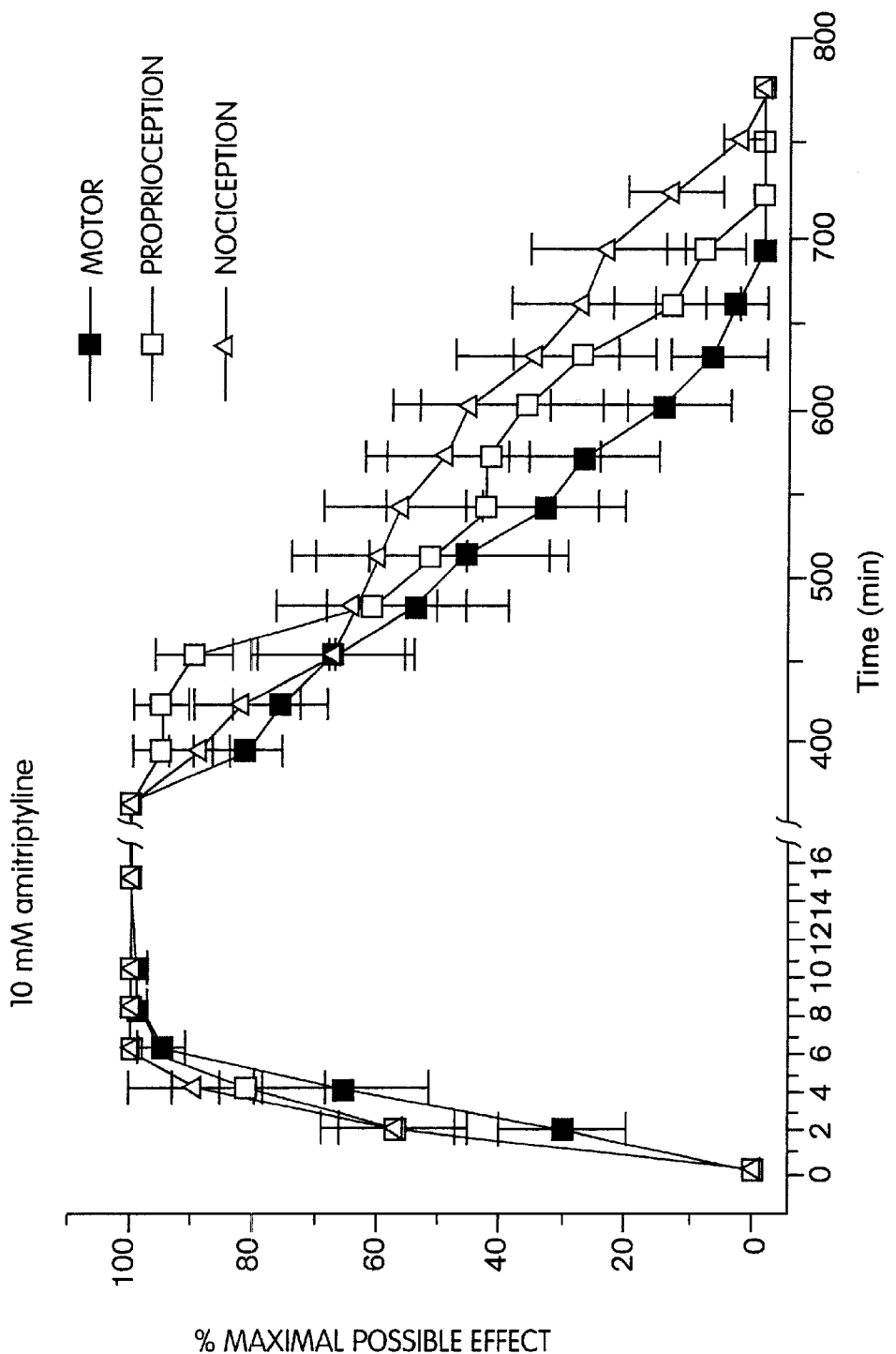

The present invention in one aspect involves the unexpected discovery that tricyclic antidepressants act as local long-acting anesthetics and analgesics and are thus useful for pain management. Surprisingly, the in vitro and in vivo activities of the compounds of the invention are significantly greater than the activities of the bupivicaine, a well known anesthetic used commonly by physicians when long-lasting anesthetic or analgesic effects are desired (See Examples). In particular, the potency of the compounds of the invention in blocking sodium channels is much greater than the local anesthetics that are known in the art.

Applicants' unexpected discovery represents the first identification that tricyclic antidepressants exhibit long-acting local anesthetic and analgesic properties. In particular, the results presented herein demonstrate that tricyclic antidepressants elicit sensory and motor block properties that are vastly improved compared to the properties of the prior art local anesthetics. Accordingly, it is believed that the compounds of the invention are particularly useful for alleviating both acute and chronic forms of pain such as back pain, postoperative pain, intractable cancer pain, rheumatoid arthritis pain, shingles, and various other forms of neuropathic pain. In addition, the compounds of the invention are believed to be useful for alleviating topical pain that is, for example, associated with a skin condition such as psoriasis and shingles.

According to one aspect of the invention, a method for inducing local anesthesia or analgesia in a subject is provided. The method involves administering locally to a subject a therapeutically effective amount of a tricyclic antidepressant (alone or together with another therapeutically useful ingredient), in an amount effective to induce local anesthesia or analgesia and alleviate pain. As used herein, "local anesthesia" refers to blocking sensory and motor function of a nerve. Blocking sensory and motor function is defined as the inhibition of action potential propagation in the neuronal membrane. The term "local analgesia" refers to blocking only the sensory function of a nerve.

Tricyclic antidepressants are a well known group of compounds. Examples of tricyclic antidepressants are: amytriptyline, amoxapine, clomipramine, desipramine, doxepin, imipramine, nortriptyline, protriptyline, trimipramine, or one of their analogues including quaternary and tertiary. In one embodiment the tricyclic antidepressant is amitriptyline or one its analogues. Analogues of amytripyline include quaternary and tertiary analogues. Examples of quaternary amytripyline analogues include but are not limited to: N-phenyl-propyl amitriptyline bromide, N-phenyl-ethyl amitriptyline bromide, or N-phenyl-methyl amitriptyline bromide. Tertiary amitriptyline analogues include but are not limited to: N-phenyl-propyl nortriptyline bromide, N-phenyl-ethyl nortriptyline bromide, or N-phenyl-methyl nortriptyline bromide. In a preferred embodiment of the invention the tricyclic antidepressant is N-phenyl-propyl amitriptyline bromide. The methods for preparing the preferred compounds of the invention are provided in the Examples and are summarized below.

The compositions of the invention are useful for alleviating pain in a subject. As used herein, "alleviating pain" refers to treating a subject so as to remove existing pain or to suppress or inhibit pain which would otherwise ensue from a pain-causing event. The treatment may be either therapeutic (while the patient is experiencing pain) or prophylactic (i.e., as preemptive anesthesia or analgesia). The treatment may be for acute or chronic pain. Examples of acute pain are: pain that can occur following trauma to body tissues, e.g., surgery, injury and so forth. Examples of chronic pain are: intractable cancer pain, rheumatoid arthritis, shingles, painful diabetic neuropathy and so forth. The method of the invention can also be applied to the treatment of pain that is associated with a skin condition such as psoriasis, eczema, and shingles. In a most preferred embodiment of the invention the pain is lower back or leg pain caused by a pathology relating to the sciatic nerve.

The tricyclic antidepressant is administered in a therapeutically effective amount sufficient to induce a long-lasting anesthetic or analgesic effect in a subject. A therapeutically effective amount is that amount which inhibits the experience of pain, lessens existing pain, prevents pain from worsening, or eliminates pain altogether. A "long-lasting" effect is defined as a pain alleviating effect lasting for at least 30 min, 60 minutes, 2 hours, 4 hours, 8 hours, 12 hours, 24 hours, 48 hours, 72 hours, or 96 hours.

In general, a therapeutically effective amount of the compounds of the invention will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days.

The therapeutics of the invention can be administered by any of the following routes including injection, infiltration anesthesia, regional anesthesia, spinal anesthesia, by inhalation or applied topically as a cream, an ointment or in the form of a patch. The injection could be intramuscular, subcutaneous, intra cavity, intraperitoneal dermal, or transdermal.

The compounds of the invention are typically administered in a pharmaceutically acceptable carrier. Such pharmaceutically acceptable carriers include components which will not significantly impair the biological properties of the compounds of the invention. Those of skill in the art can readily determine the various parameters and conditions for producing such pharmaceutical preparations without resort to undue experimentation.

Preparations for local parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl-oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. As would be apparent to those of ordinary skill in the art, the compounds of the invention alternatively can be delivered using controlled release drug delivery systems. Preferably such systems are biodegradable and bioerodible. Preservatives and other additives may also be present such as, for example, antimicrobials, anti-oxidants, chelating agents, and inert gases and the like. The compounds of the invention may also be used in combination with other therapeutic agents, such as anti-inflammatory agents. In general, the therapeutics of the invention are sterile preparations and can be sterilized, for example, by gamma irradiation. The pharmaceutical composition can be contained in an implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/03307 describes a biocompatible, preferably biodegradable polymeric matrix for sustained release of an exogenous agent in the patient. In accordance with the instant invention, the compositions described herein are encapsulated or dispersed within the biocompatable, preferably biodegradable polymeric matrix disclosed in PCT/US/03307. The polymeric matrix preferably is in the form of a micro particle such as a micro sphere (wherein the composition is dispersed throughout a solid polymeric matrix) or a microcapsule (wherein the composition is stored in the core of a polymeric shell). Other forms of the polymeric matrix for containing the composition include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used. The polymeric matrix composition can be selected to have both favorable degradation rates and also to be formed of a material which is bioadhesive, to further increase the effectiveness of transfer when the devise is administered to a mucosal or other surface. The matrix composition also can be selected not to degrade, but rather, to release by diffusion over an extended period of time.

Both non-biodegradable and biodegradable polymeric matrices can be used to deliver the compositions of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers. In general, the compositions of the invention are delivered using the bioerodible implant by way of diffusion, or more preferably, by degradation of the polymeric matrix.

Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in *Macromolecules*, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described therapeutic agents for use as a medicament, methods for preparing the medicament and methods for the sustained release of the medicament in vivo.

When the compositions of the invention are to be used to alleviate epidural or intrathecal pain, injection or administration of the compositions through a catheter is the most simple mode of administration. The compounds of the invention can be administered, for example, in an aqueous medium, such as an isotonic solution, or in a non-aqueous medium, such as glycerol or an oil. Alternatively, the compounds of the invention can be administered as an injectable suspension to achieve a more prolonged effect. The preferred medium for intrathecal injection is isotonic dextrose. Other exemplary pharmaceutically acceptable intrathecal carriers include hypobaric (e.g., 50% normal saline) and hyperbaric (e.g., 5–8% glucose) solutions. (See, e.g., Neural Blockade, ed., Cousins & Bridenbaugh, pp. 213–251 (1988). In general, the compounds of the invention are present in an intrathecal formulation in an amount ranging from about 0.1% to about 10% by weight, based upon the total weight of the composition. Preferably, the compounds of the invention are present in an amount ranging from about 0.25% to about 2.5% by weight and, most preferably, the compounds are present in an amount ranging from about 0.5% to about 1% by weight. In some embodiments, it is preferred that the compounds of the invention be formulated in a pharmaceutically acceptable intrathecal or topical carrier that is not suitable for oral administration.

When the compositions of the invention are to be used to alleviate a topical pain, the compounds can be administered as a pure dry chemical (e.g., by inhalation of a fine powder via an insufflator) or as a pharmaceutical composition further including a pharmaceutically acceptable topical carrier. Thus, the pharmaceutical compositions of the invention include those suitable for administration by inhalation or insufflation or for nasal, intraocular or other topical (including buccal and sub-lingual) administration.

For administration to the upper (nasal) or lower respiratory tract by inhalation, the compounds of the invention can be delivered from an insufflator, nebulizer or a pressurized pack or other convenient means of delivering an aerosol spray. Alternatively, the compounds of the invention can be delivered as a dry powder composition containing, for example, the pure compound together with a suitable powder base (e.g., lactose, starch).

For intra-nasal administration, the compounds of the invention can be administered via nose drops, a liquid spray, such as via a plastic bottle atomizer or metered-dose inhaler. Exemplary atomizers are known to those of ordinary skill in the art. Drops, such as eye drops or nose drops, can be formulated with an aqueous or non-aqueous base which optionally further includes one or more dispersing agents, solubilizing agents or suspending agents. Apparatus and methods for delivering liquid sprays and/or drops are well known to those of ordinary skill in the art.

For topical administration to the eye, nasal membranes or to the skin, the compounds according to the invention may be formulated as ointments, creams or lotions, or as a transdermal patch or intraocular insert or iontophoresis. For example, ointments and creams can be formulated with an aqueous or oily base alone or together with suitable thickening and/or gelling agents. Lotions can be formulated with an aqueous or oily base and, typically, further include one or more emulsifying agents, stabilizing agents, dispersing agents, suspending agents, thickening agents, or coloring agents. (See, e.g., U.S. Pat. No. 5,563,153, entitled "Sterile Topical Anesthetic Gel", issued to Mueller, D., et al., for a description of a pharmaceutically acceptable gel-based topical carrier.)

In general, the compounds of the invention are present in a topical formulation in an amount ranging from about 0.01% to about 30.0% by weight, based upon the total weight of the composition. Preferably, the compounds of the invention are present in an amount ranging from about 0.5 to about 30% by weight and, most preferably, the compounds are present in an amount ranging from about 0.5 to about 10% by weight. In one embodiment, the compositions of the invention comprise a gel mixture to maximize contact with the surface of the localized pain and minimize the volume and dosage necessary to alleviate the localized pain. GELFOAM® (a methylcellulose-based gel manufactured by Upjohn Corporation) is a preferred pharmaceutically acceptable topical carrier. Other pharmaceutically acceptable carriers include iontophoresis for transdermal drug delivery.

In one aspect of the invention, the compounds of the invention are formulated in a composition to alleviate pain in the oral cavity. An exemplary pharmaceutically acceptable topical carrier for the sustained release of a pain relieving substance in the oral cavity is a polyvinyl alcohol matrix such as that described in U.S. Pat. No. 5,520,924, entitled "Methods and articles for administering drug to the oral cavity", issued to Chapman, R., et al. Alternative formulations suitable for topical administration in the mouth or throat include lozenges comprising the compound(s) of the invention in a flavored base, usually sucrose and acacia or tragacanth; pastilles comprising the compound(s) in an inert base such as gelatin and glycerin or sucrose and acacia; and mouthwashes comprising the active ingredient in a suitable liquid carrier. Other suitable carriers for delivery to the oral cavity or other topical surface and/or for the sustained release of a pain alleviating compound are known to one of ordinary skill in the art.

In general, the compounds of the invention described herein can be administered in accordance with known methods for administering tricyclic antidepressants. Because the quaternary and tertiarty amitriptyline derivatives compounds described herein are significantly more potent than the base compounds from which they are derived, a lower dosage can be administered to a subject to induce a therapeutically effective result.

In one embodiment of the invention, a composition including the tricyclic antidepressant amitriptyline is provided. Preferably, the composition further includes a pharmaceutically acceptable carrier and the amitriptyline in a therapeutically effective amount. In one embodiment of the invention, the composition includes a quaternary or tertiary analogue of amitriptyline. Exemplary quaternary amytripyline analogues include but are not limited to: N-phenyl-propyl amitriptyline bromide, N-phenethyl amitriptyline bromide, or N-phenyl-methyl amitriptyline bromide. Exemplary tertiary amitriptyline analogues include but are not limited to: N-phenyl-propyl nortriptyline bromide, N-phenethyl nortriptyline bromide, or N-phenyl-methyl nortriptyline bromide. Preferably, the composition further includes a pharmaceutically acceptable carrier and a quaternary or tertiary amitriptyline in a therapeutically effective amount. In one embodiment of the invention the tricyclic antidepressant is N-phenyl-propyl amitriptyline bromide. Preferably, the composition further includes a pharmaceutically acceptable carrier and the phenyl-propyl amitriptyline bromide in a therapeutically effective amount. The composition may also consist of other amitriptyline analogues with other groups attached to the quaternary ammonium or tertiary analogue amitriptyline. Such groups can include: an alkyl, aryl or cyclic functional group containing from four to twelve carbon atoms (e.g., heptyl-, octyl-, nonyl-, decyl-, aryl-, cyclopentyl-, cyclohexyl-, propylphenyl-, butyl-phenyl-, hexylphenyl-), provided that the derivative compound is amphipathic. The foregoing chemical terms have their common meaning known to one of ordinary skill in the art. The above-noted functional groups that can be used can be saturated or unsaturated, straight-chained or branched. Optionally, one or more hydrogen atoms of the functional group can be replaced by a substituent group, such as a chloride, an amino group or a thio group.

N-phenyl-propyl amitriptyline is synthesized from amitriptyline in accordance with the procedure provided in the Example. Of course, other salts of this compound and other amitriptyline analogues alternatively can be used for practicing the invention. For example, in addition to the bromide salt, chloride, phosphate, sulfate, citrate, and acetate salts can be used.

The ability of one of the preferred amitriptyline analogues, N-phenyl-ethyl amitriptyline, to elicit sciatic nerve block of sensory and motor functions in vivo was tested in rats as described in the Examples. The results of the Examples demonstrate that N-phenyl-ethyl amitriptyline exhibits the requisite local anesthetic properties to render this agent particularly useful as a long-acting local anesthetic for pain management in humans. In particular, the results demonstrate that N-phenyl-ethyl amitriptyline is a potent sodium channel blocker in vitro and produced strong tonic and use-dependent inhibition of sodium channels in vitro.

The animal model used in the Examples is illustrative of an early stage of neuropathic pain and is, in particular, predictive of neuropathic and chronic pain in humans. The animal model experiments described in the Examples are predictive of pain conditions and can be used to predict the efficacy of the compounds of the invention in alleviating acute as well as chronic pain in humans. These results suggest a particularly preferred utility for N-phenyl-ethyl, amitriptyline and N-phenyl-propyl amitriptyline for pain management.

EXAMPLES

Chemicals

Amitriptyline was purchased from Sigma Chemical Co. (St. Louis, Mo.); bupivacaine was a gift from Astra USA, Inc. (Westborough, Mass. ). For the electrophysiological experiments amitriptyline and bupivacaine were dissolved in dimethyl sulfoxide at 100 mM and were diluted shortly before the experiments. For the sciatic nerve blockades, amitriptyline and bupivacaine hydrochloride were dissolved in 0.9% sodium chloride.

Design and Organic Synthesis of Amitriptyline Derivatives

Organic synthesis of amitriptyline derivatives was according to a method described by Wang et al. (Biophysical Journal 67:1851–1860; 1994).

Sciatic Nerve Injections

Male Sprague-Dawley rats were purchased from Taconic Farm, Inc., Germantown, N.Y., and kept in animal housing facilities with controlled humidity (20–30% relative humidity), room temperature, and a 12-h (6:00 AM- 6:00 PM) light-dark cycle. Rats were handled before behavioral testing to familiarize them with the experiment and to minimize stress-induced analgesia. At the time of injections, animals weighed approximately 250–300 g. The experimenter was blinded to the drug/concentration used.

For sciatic nerve blockade, rats were lightly anesthetized by inhalation of sevoflurane and the landmarks (greater trochanter and ischial tuberosity) of the left hind limb were localized. A volume of 0.2 ml of either 15.4 mM (corresponding to the frequently used clinical concentration of 0.5%) bupivacaine hydrochloride (n=6), pH 6.5, 5 mM amitriptyline (n=8), or 10 mM amitriptyline (n=7), pH 4.9, was injected in immediate proximity to the sciatic nerve with a 27-G hypodermic needle attached to a tuberculin syringe as described, and the rat was observed for the development of sciatic nerve block, indicated by complete paralysis of the hind limb. The right hind limb was used as a control.

Neurobehavioral Examination

Neurobehavioral examination consisted of evaluation of motor function, proprioception, and nocifensive reaction immediately before inhalation of sevoflurane, at 2, 4, 6, 8, 10, 15, 20, 25, 30, 45, and 60 minutes after the injection, and then at 30-minute intervals until 750 minutes (12.5 hours). The following is a brief description of the neurobehavioral examination.

Motor function. Motor function was evaluated by measuring the "extensor postural thrust" of the hind limbs. The rat was held upright with the hind limb extended so that the body's weight was supported by the distal metatarsus and toes. The extensor thrust was measured as the gram force applied to a digital platform balance (Ohaus Lopro, Fisher Scientific, Florham Park, N.J.), the force that resists contact of the platform by the heel. The preinjection control value (range 130–165 gram) was considered 0% of the maximal possible effect (MPE). The reduction in this force, representing reduced extensor muscle contraction due to motor blockade, was calculated as a percentage of the control force. A force less than 20 grams (also referred to as weight of the "flaccid limb") was considered 100% MPE.

Proprioception. Proprioception evaluation was based on resting posture and postural reactions ("tactile placing" and "hopping"). The functional deficit was graded as 3 (normal) or 0% MPE, 2 (slightly impaired), 1 (severely impaired), and 0 (complete) or 100% MPE. Keeping the rat in a normal resting posture with the toes flexed and the dorsi of the feet placed on the supporting surface, we evaluated tactile placing as the ability to reposition the toes.

Hopping response was evoked by lifting the front half of the animal off the ground and then lifting one hind limb at a time off the ground so that the animal moved laterally. This process normally evokes a prompt hopping with the weight-bearing limb in the direction of movement to avoid falling over. A predominantly motor impairment causes a prompt but weaker than normal response. Conversely with a predominantly proprioceptive blockade, delayed hopping is followed by greater lateral hops to avoid falling over or, in case of full blockade, no hopping at all.

Nocifensive reaction. Nocifensive reaction was evaluated by the withdrawal reflex and/or vocalization to pinch of a skin fold over the lateral metatarsus (cutaneous pain) and of the distal phalanx of the fifth toe (deep pain). Nocifensive reaction was graded 4 (normal or 0% MPE), 3 (25% MPE), 2 (50% MPE), 1 (75% MPE), and 0 (absent or 100% MPE).

Whole-Cell Voltage Clamp Experiments and Cell Culture

The whole-cell configuration of the patch-clamp technique was used to record macroscopic $Na^+$ currents at room temperatures ranging from 21 to 23 degrees Celsius. Command voltages were controlled by pCLAMP software (Axons Instruments, Inc., Foster City, Calif.) and delivered by a List-EPC7 patch clamp amplifier (List-Electronic, Darmstadt/Eberstadt, Germany). After the establishment of whole-cell configuration, cells were dialyzed for 30 minutes before data were acquired. Data were filtered at 5 kHz, sampled at 50 kHz, collected, and stored with pCLAMP software. Leak and capacitance currents were subtracted by P/4 protocol, which was not applied in the use-dependent block of $Na^+$ currents. Pipette electrodes were filled with an internal solution containing (in mM) 100 NaF, 30 NaCl, 10 ethylene glycol-bis($\beta$-aminoethylether)N,N,N',N'-tetraacetic acid (EGTA), and 10 hydroxyethylpiperazineethane sulfonic acid (HEPES) titrated with CsOH to pH 7.2. The external solution consisted of (in mM) 85 choline Cl, 65 NaCl, 2 $CaCl_2$, and 10 HEPES titrated with tetramethylammoniumhydroxide to pH 7.4.

Rat clonal pituitary $GH_3$ cells were purchased from the American Type Culture, Collection (Rockville, Md.). Cells were split twice a week and maintained in Dulbecco's modified Eagle's medium supplemented with penicillin/streptomycin (1%) and heat-inactivated fetal bovine serum (10%). The 35 mm-culture dishes in which the cells were grown were also used as a recording chamber.

An unpaired Student's t test or a one-way analysis of variance was used to calculate the significance of difference between the 50% inhibitory concentration, $IC_{50}$, of bupivacaine and amitriptyline or the inhibition of $Na^+$ current at the $60^{th}$ pulse (control bupivacaine, and amitriptyline). An unpaired Student's t test was also used to detect significant differences among the proprioceptive, motor, and sensory functions of the animals after bupivacaine or amitriptyline injection (Origin, Microcal Software, Inc., Northhampton, Mass.). Statistical significance was defined as $p<0.05$.

Results

Rat Sciatic Nerve Blockade

All rats developed a complete sciatic nerve blockade following the amitriptyline injection. The detailed time course of onset and recovery of blockade is shown in FIGS. 1A, B, C. All animals recovered promptly from sevoflurane inhalation anesthesia (~1–1.5 min), allowing also to examine the onset of the block. No rats showed evidence of pain behavior irritation like biting or licking the extremity.

Onset. Full nocicptive, motor, and proprioceptive blockade was achieved at 4 min with bupivacaine, at 6 min with 10 mM amitriptyline, but not until 30 min with amitriptyline at a concentration of 5 mM.

Figure 2:
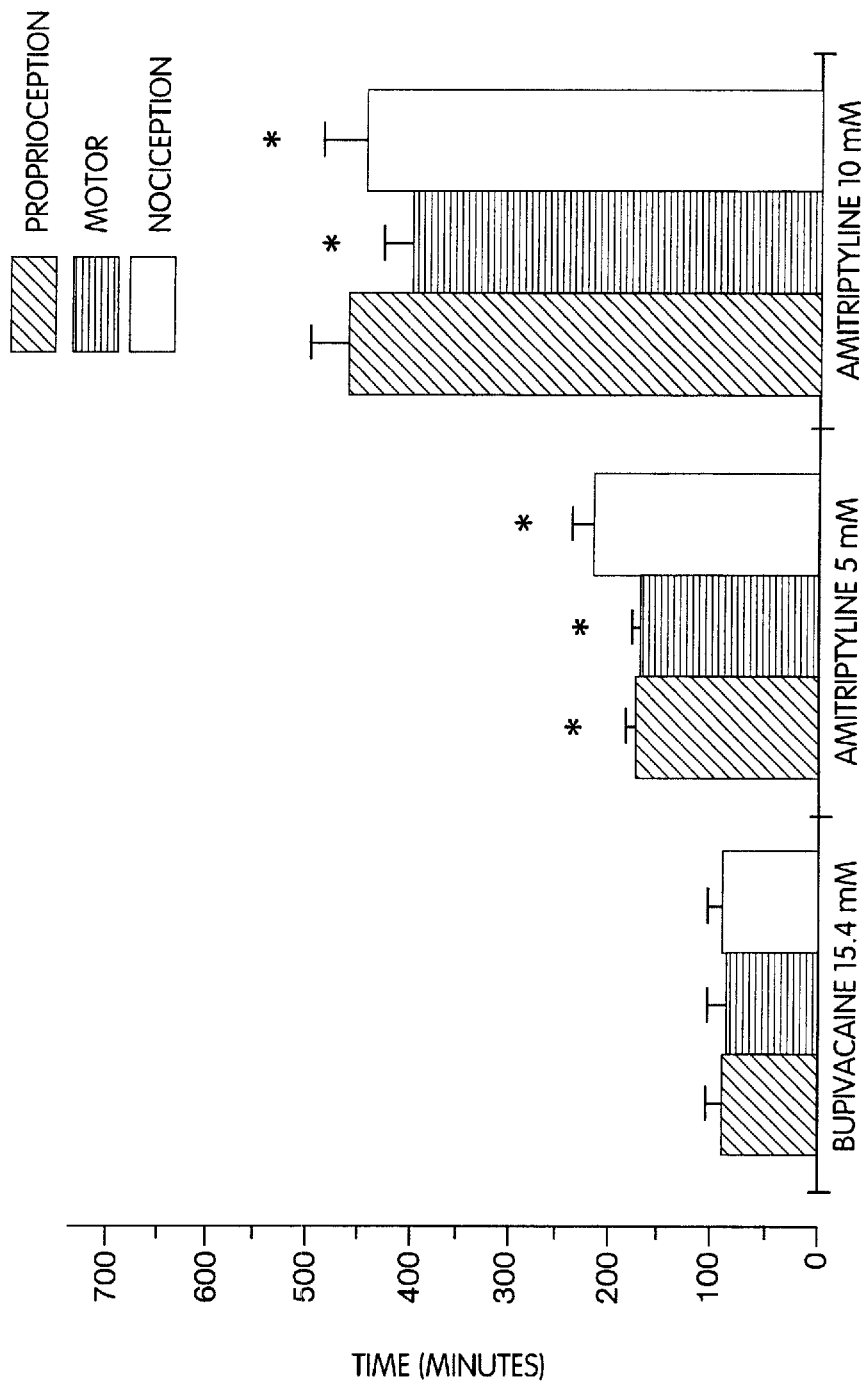
FIG. 2. Histogram of the time of complete blockade of rat sciatic nerve propioceptive, motor, and nociceptive functions following the injection of 15.4 mM bupivacaine, 5 mM amitriptyline, or 10 mM amitriptyline.

Duration of complete blockade. In the bupivacaine group, differential blockade was not observed (90±13.4 min for blockade of proprioception and nociception, 87.5±14.7 min for motor blockade). In the 5 and 10 mM amitriptyline groups, nociceptive blockade was statistically significantly longer than motor blockade (217.5±19.4 and 454.8±38.4 versus 168.7±7.9 and 402.9±27.7 min, respectively). However, in the amitriptyline 10 mM group, the duration of complete blockade for proprioception was slightly longer (467.1+35.8) than for nociception (454.3±38.4), but this difference was not statistically significant (FIG. 2).

Figure 3:
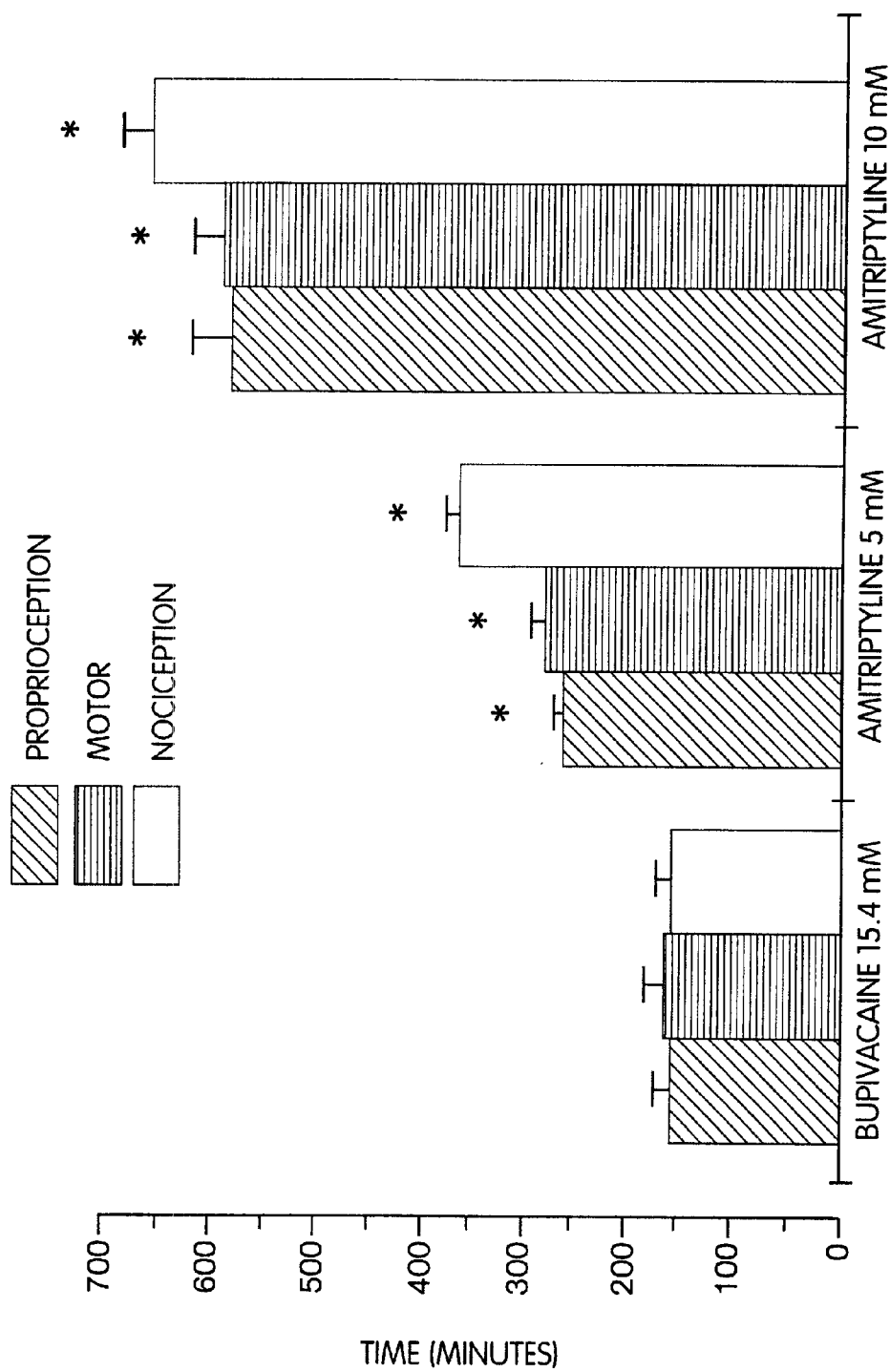
FIG. 3. Histogram of the time to full recovery of rat sciatic nerve propioceptive, motor, and nociceptive functions following the injection of 15.4 mM bupivacaine, 5 mM amitriptyline, or 10 mM amitriptyline.

Duration to full recovery. In contrast to the bupivacaine group, where all functions tested were recovering roughly at the same time, for the animals in the amitriptyline groups recovery of nociceptive blockade was significantly delayed compared with motor and proprioceptive blockade. The time to full recovery of functions for amitriptyline at 5 and 10 mM was 352.5±12.4 and 655.7±27.3 for nociception, 270±13.9 and 582.6±32.6 for motor function, 255.0±11.3 and 578.6±39.7 min for proprioception and for bupivacaine 155.0:L9.2, 160.0±6.3 and 155.0±9.2 min, respectively (FIG. 3). Therefore, within both amitriptyline groups, nociceptive function was blocked significantly longer than motor and porprioceptive function.

Single Cell Studies

Figure 4A:
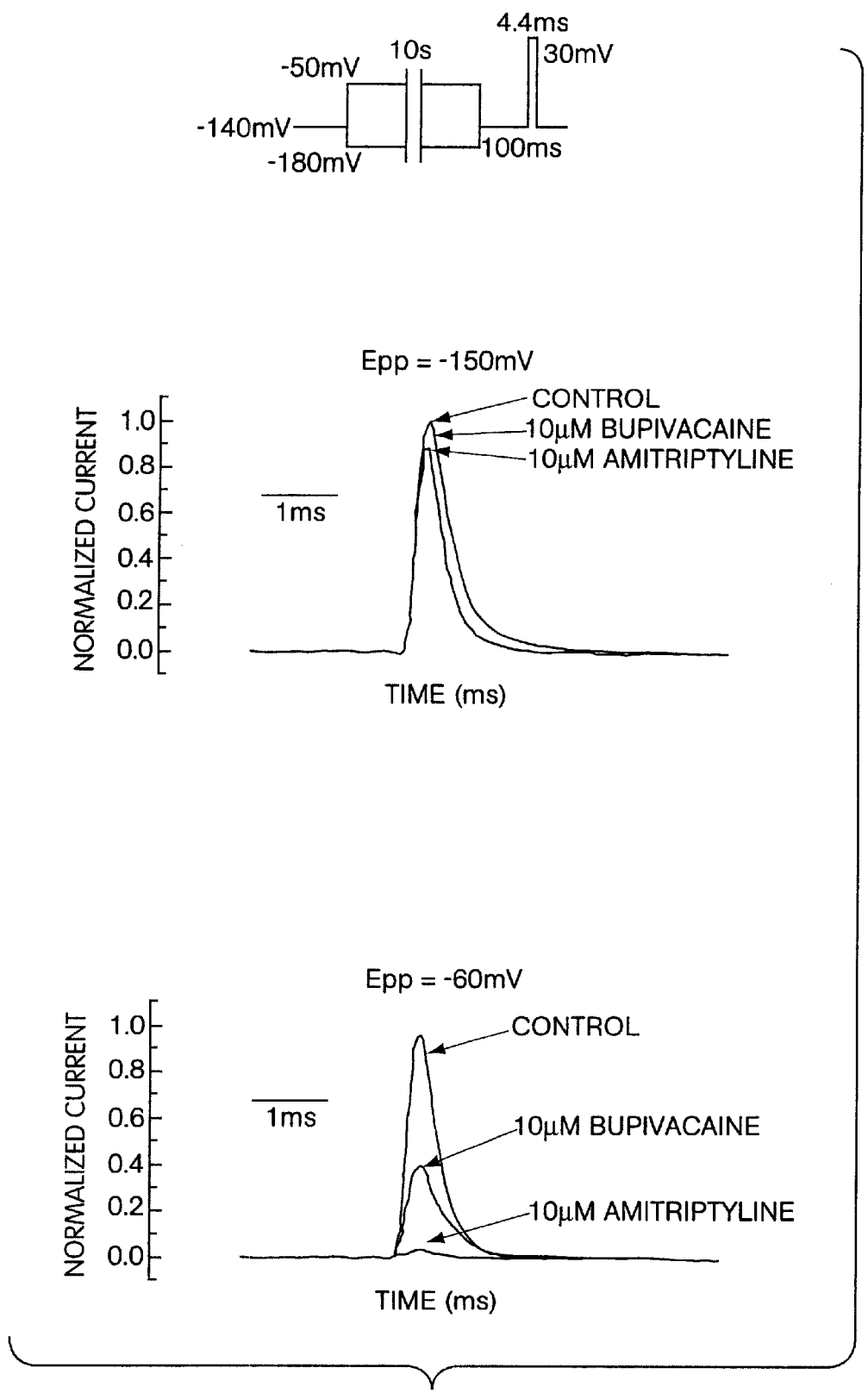
FIG. 4. Voltage-dependent blockade with 10 μM amitriptyline, 10 μM bupivacaine or with no drug 1 (control). (A) Traces of pulse protocol and representative tracings for the resting state and for the inactivated state. (B) Graph of the normalized $Na^+$ current availability function for 10 μM amitriptyline and 10 μM and for control (no drug).
Figure 5A:
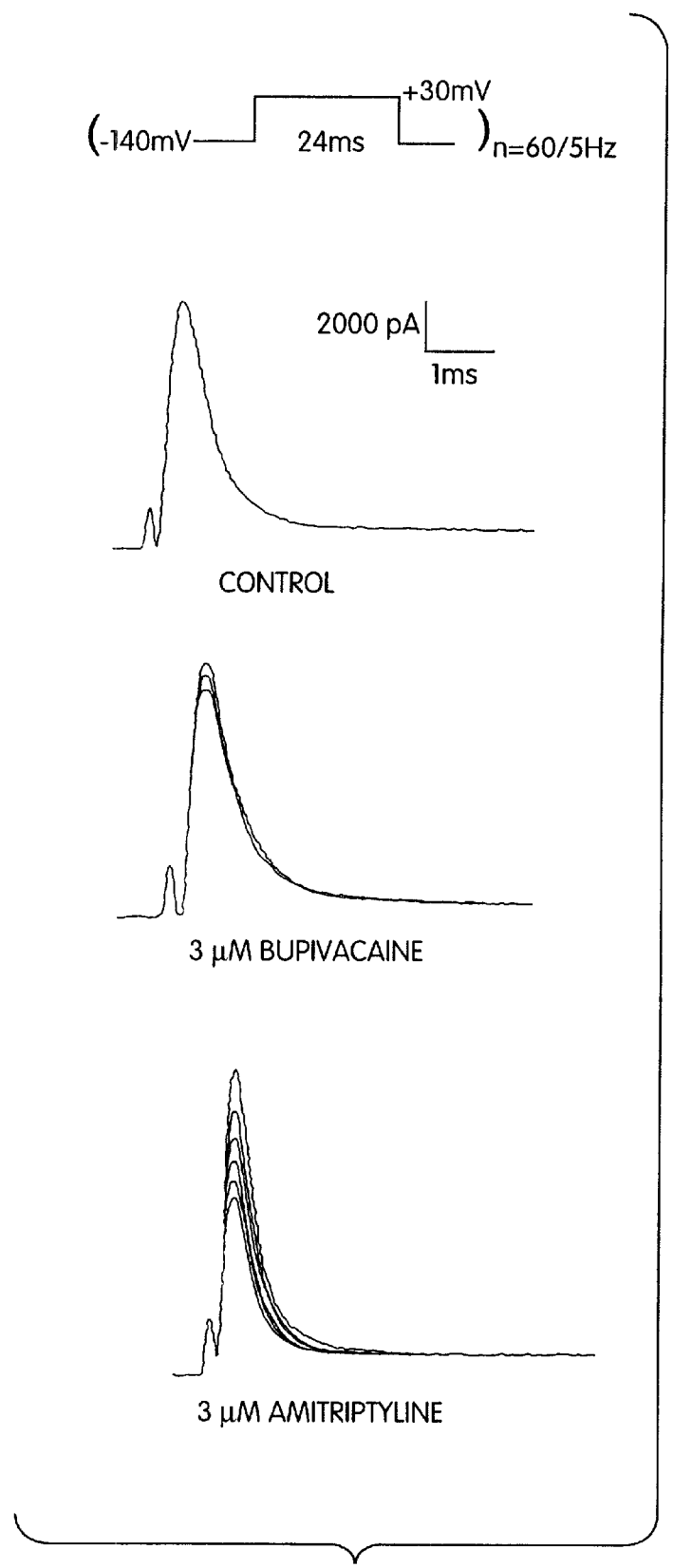
FIG. 5. Potency of amitriptyline and bupivacaine in producing voltage-dependent blockade in the resting and inactivated state of the $Na^+$ channels in patch clamped single cells. (A) Traces of pulse protocol and representative tracings for the resting state and for the inactivated state. (B) Dose response curves showing that amitriptyline has a much higher affinity (10×more potent) to the inactivated state than bupivacaine.
Figure 5B:
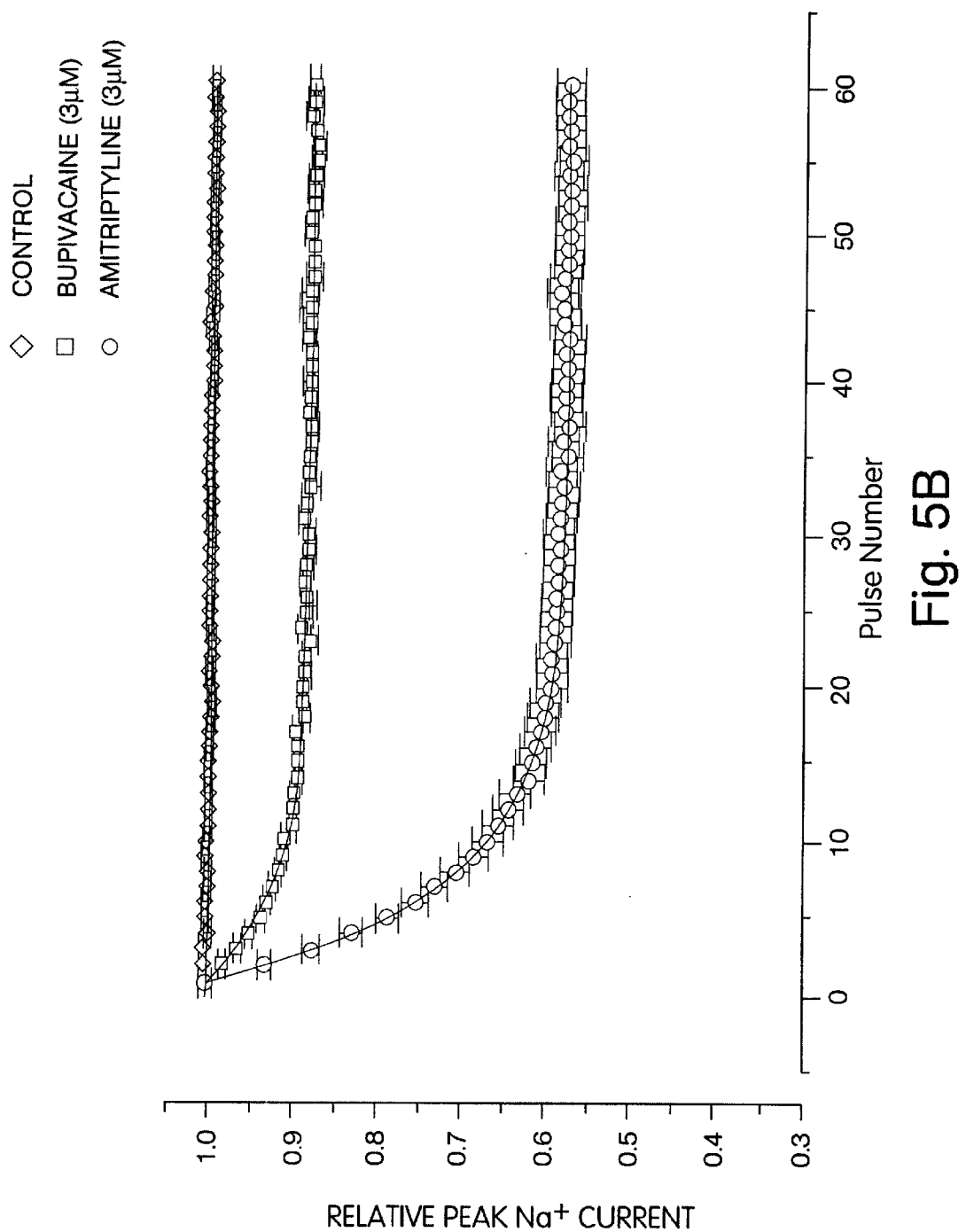
Figure 6:
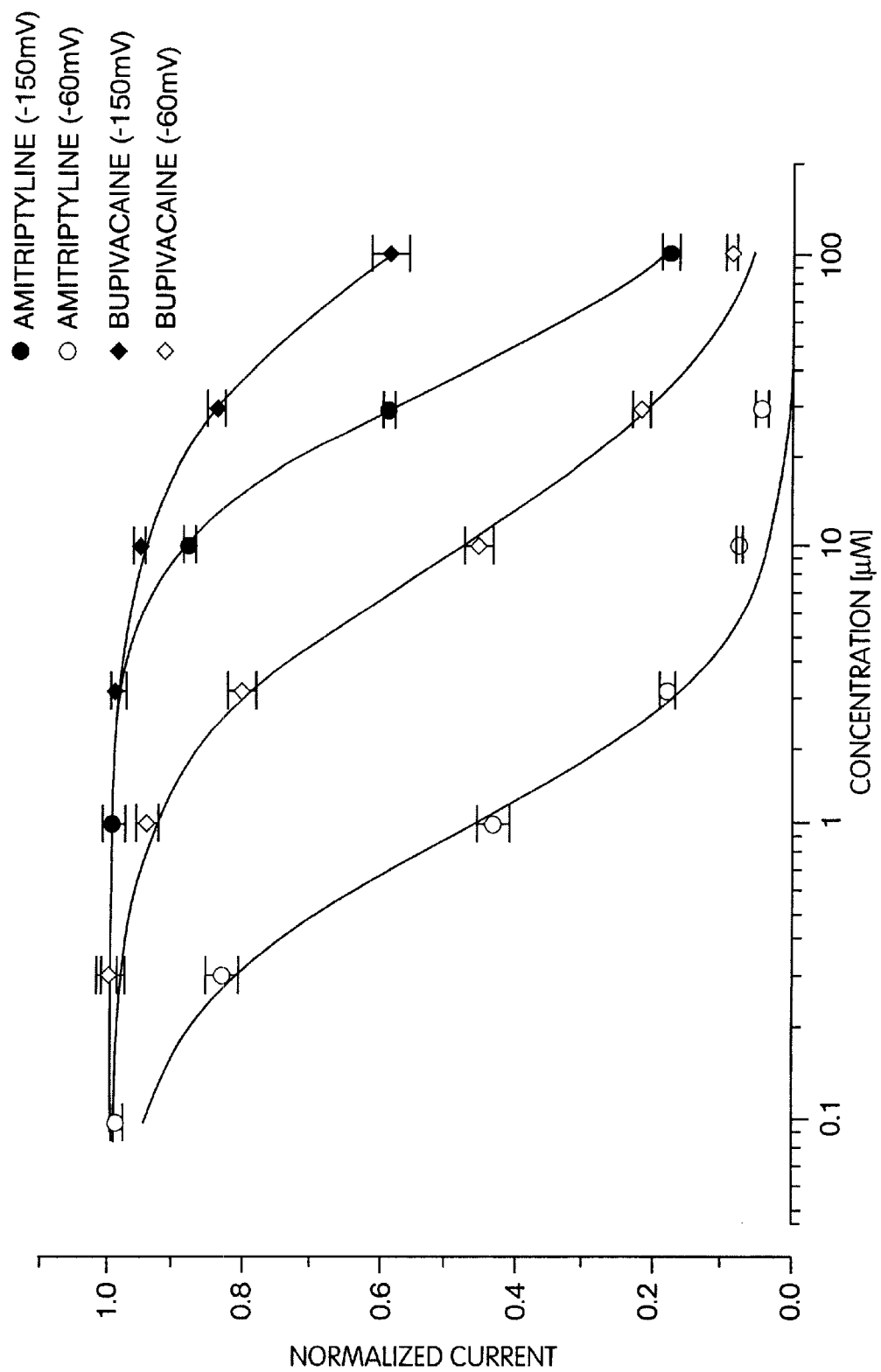
FIG. 6. Graph of the use-dependent block of $Na^+$ current produced by amitriptyline and bupivacaine in patch-clamped cells.

To determine the voltage-dependent blockade by amitriptyline or bupivacaine, a prepulse or conditioning pulse at various voltages and long enough to permit the drug-channel binding interaction to reach its steady-state level was applied (pulse protocol and representative tracings are shown in FIG. 4A). In order to determine the potency of amitriptyline and bupivacaine for the resting and inactivated states, dose-response curves were subsequently constructed at holding potentials of −150 mV and −60 mV, respectively (FIG. 5). Finally, additional blockade provoked by high-frequency stimulation (use dependent blockade) was investigated (pulse protocol and representative tracings are shown in FIG. 6A).

Figure 4B:
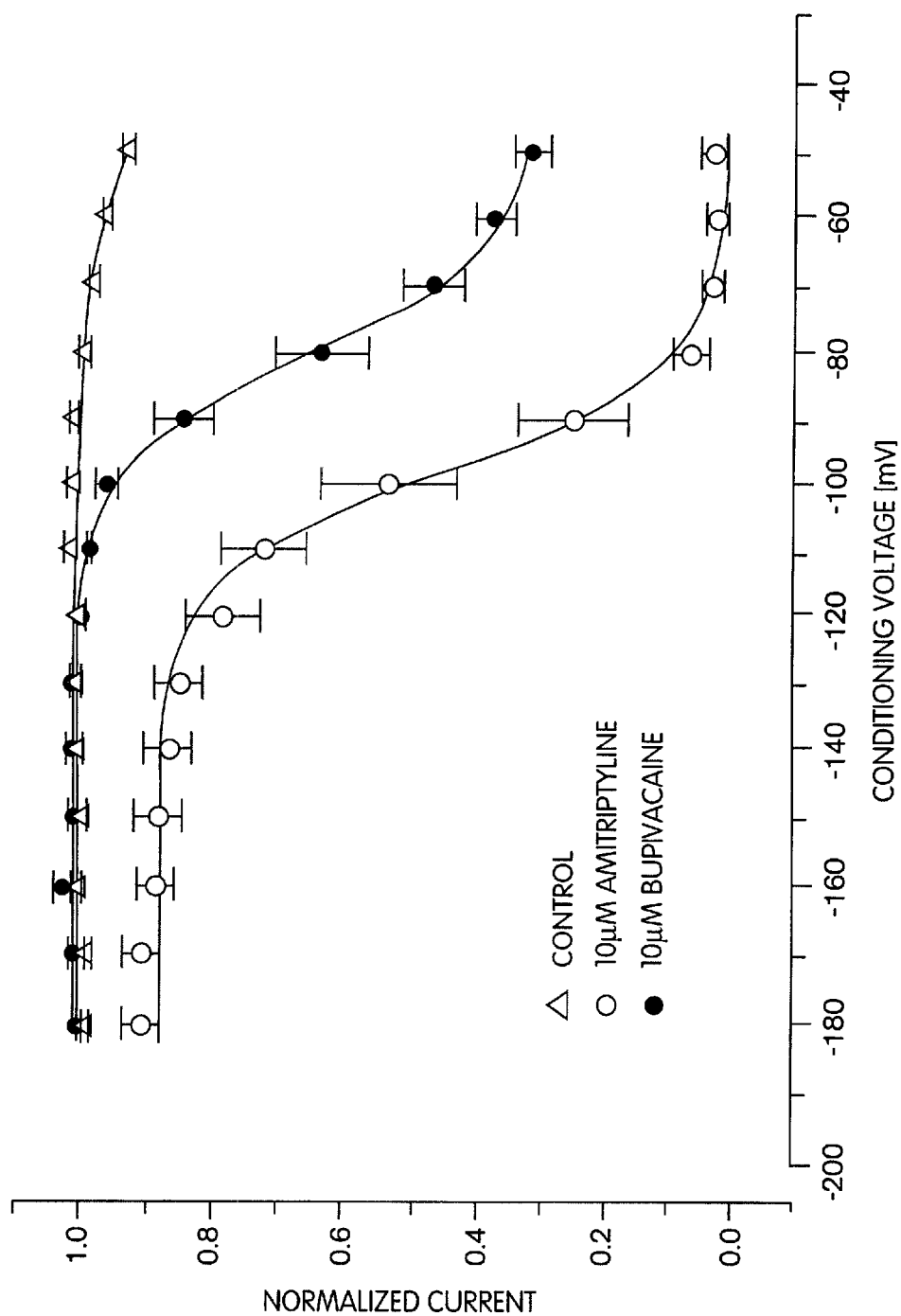

Voltage-dependent blockade. The blocking characteristics at different voltages for rat clonal pituitary $GH_3$ cells with drug application (amitriptyline or bupivacaine) or without drug (control) are shown in FIG. 4B. When no drug was applied, prepulses at a potential more positive than −90 mV began to induce slow inactivation, resulting in a decrease of peak $Na^{30}$ currents of up to ~10%. Amitriptyline at a concentration of 10 μM causes ~15% of all channels to be blocked in the resting state at a conditioning pulse of −150 mV compared with >95% of $Na^+$ channels blocked in the inactivated state at a conditioning pulse of −60 mV. On the other hand, when 10 μM concentration of bupivacaine was applied, a conditioning pulse of 60 mV caused >70% of all channels to be blocked in the inactivated state, but at −150 mV essentially none of the channels in the resting state were blocked by this drug. As shown in FIG. 4B, both drugs reach asymptote at a conditioning voltage of −150 and −60 mV. We therefore chose these potentials to determine the affinity for both drugs for the resting state at −150 mV and for the inactivated state at −60 mV.

Affinity for resting and inactivated channels. Dose-response curves revealed that in in the inactivated state (−60 mV) amitriptyline was ~10× more potent, and in the resting state (−150 mV) ~15× more potent than bupivacaine (FIG. 5). The 50% inhibitory concentrations ($IC_{50}S$) of amitriptyline and bupivacaine at −150 mV were 140.6±4.4 and 9.5±0.6 and at −60 mV 0.9±0.1 and 9.5±0.6 μM, respectively (p<0.5). The Hill coefficient was calculated for amitriptyline and bupivacaine in the resting state as 1.56±0.03 and 1.12±0.04, and in the inactivated state as 1.35±0.15 and 1.16±0.08, respectively.

Use-dependent blockade. High-frequency stimulation at 5 Hz produced no measurable blockade of $Na^+$ currents in the control. External perfusion of the cells were with a 3 μM concentration of bupivacaine caused an additional ~14% blockade, whereas a 3 μM concentration of amitriptyline caused ~50% blockade (FIG. 6B). The differences among these three groups are statistically significant. Both drugs reach the new steady state relatively fast (well before the 60th pulse).

Washout for both drugs at all concentrations and with all protocols was complete but qualitatively slower with amitriptyline (within 5 min) than with bupivacaine (within 3 min).

Testing the Effect of Amitriptyline Derivatives on Sciatic Nerve Blockade

Figure 7:
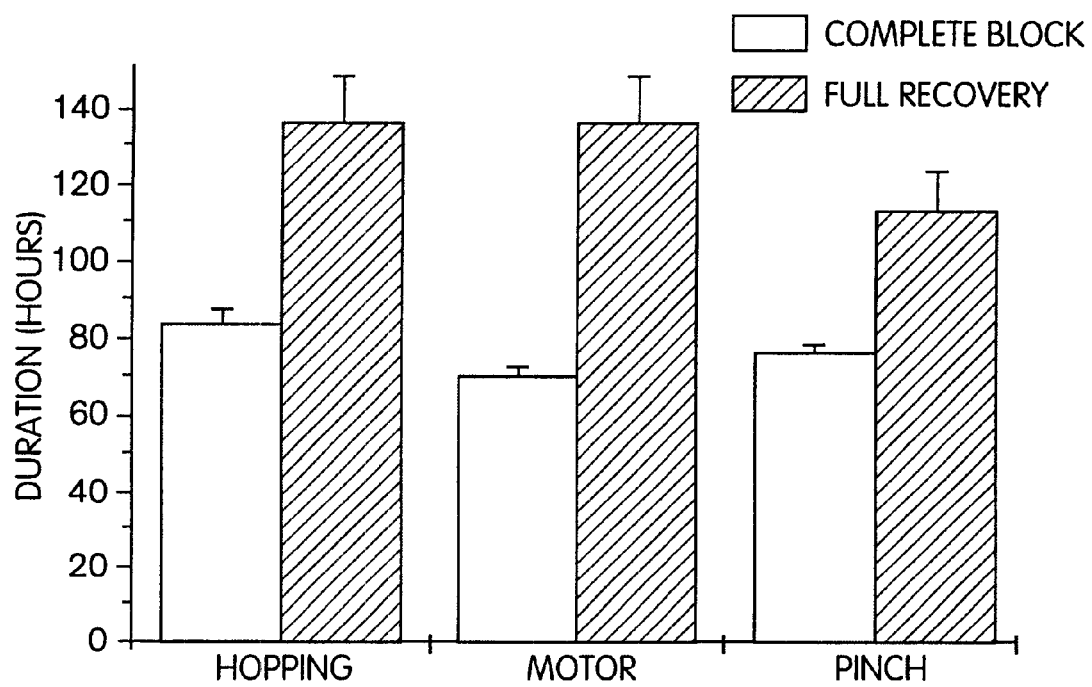
FIG. 7. Histogram of the effect of 5 mM N-phenyl-ethyl amitriptyline on sciatic nerve blockade.

We focused primarily on the design of compounds that are potentially applicable to in vivo use such as N-phenyl-ethyl amitriptyline and N-phenyl-propyl amitriptyline which we have already custom synthesized and tested in our in vivo model. To reiterate the rationale for our drug design, we have provided evidence that (1) amphipathic quaternary ammonium derivatives remain as potent $Na^+$ channel blockers, perhaps more potent than their parent drugs, and (2) amphipathic derivatives are effective in blocking nerve function in vivo. Since amphipathic drugs do not pass through membrane barriers or blood vessels rapidly, even the danger of cardiotoxicity and CNS toxicity via accidental injection of drug into bloodstream can be minimized. These findings are the bases of our drug design. FIG. 7 shows that a single injection of N-phenyl-ethyl amitriptyline at 5 mM into the rat sciatic notch elicits an ultralong duration of complete sciatic nerve block of 70–80 hrs (~3 days). Full recovery of function was found within 5–6 days. Barring from neurotoxicity and cardiotoxicity this drug extends the duration of complete nerve block of its parent drug by more than 10-fold (5 vs. 70 hrs).

What is claimed is:

1. A method for inducing local anesthesia in a subject comprising administering locally to a subject in need of such a treatment a tricyclic antidepressant in an amount effective to block sensory and motor function of a nerve(s) at the site of administration of the tricyclic antidepressant.

2. The method to claim 1 wherein the tricyclic antidepressant is amitriptyline.

3. The method to claim 1 wherein the tricyclic antidepressant is an amitriptyline analogue.

4. The method to claim 1 wherein the tricyclic antidepressant is represented in the following formula:

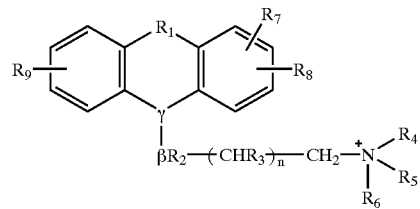

wherein
$R_1$ equals C—C, C—O, or C═C
γ-β equals C═C, N—C or CH—C
n equals 1,2, 3,4, 5, or 6
$R_2$ equals H or $H_2$
$R_3$ equals H or $CH_3$ or nothing
$R_4$ equals H or $R_6$
$R_5$ equals H or $R_6$
$R_6$ equals $(C_1–C_8)$ alkyl, $(C_1–C_8)$ substituted alkyl, $(C_1–C_8)$ alkenyl, $(C_1–C_8)$ substituted alkenyl, $(C_1–C_8)$ alkynyl, ($C_1$–$C_8$) substituted alkynyl (wherein the subtituents can be ($C_1$–$C_4$) alkyl, ($C_1$–$C_4$) substituted alkyl, ($C_1$–$C_4$) alkenyl, ($C_1$–$C_4$) substituted alkenyl, ($C_1$–$C_4$) alkynyl, ($C_1$–$C_4$) substituted alkynyl), or $R_6$ is nothing, $R_7$ equals H or Cl $R_8$ equals H or Cl $R_9$ equals H or Cl, and wherein when $R_1$ equals C═C, at least one of $R_4$, $R_5$, and $R_6$ is 2, 3, 4, 5, 6, 7, 8, 9, 10, 11, or 12 carbons in length.

5. The method to claim 1 wherein the tricyclic antidepressant is a quaternary analogue of amitriptyline selected from the group consisting of: N-phenyl-propyl amitriptyline bromide, N-phenyl-ethyl amitriptyline bromide, or N-phenyl-methyl amitriptyline bromide.

6. The method to claim 1 wherein the tricyclic antidepressant is a tertiary analogue of amytriptyline selected from the group consisting of: N-phenyl-propyl nortriptyline bromide, N-phenyl-ethyl nortriptyline bromide, or N-phenyl-methyl nortriptyline bromide.

7. The method to claim 1 wherein the tricyclic antidepressant induces anesthesia for at least 30 minutes, 60 minutes, 2 hours, 4 hours, 8 hours, 12 hours, 24 hours, 48 hours, 72 hours, or 96 hours.

8. The method to claim 1 wherein the site of administration is the lower back.

9. The method to claim 1 wherein the nerve is the sciatic nerve.

10. The method to claim 1 wherein the tricyclic antidepressant is administered by injection.

11. The method to claim 10 wherein the tricyclic antidepressant is injected intramuscularly.

12. The method to claim 10 wherein the tricyclic antidepressant is injected subcutaneously.

13. The method to claim 10 wherein the tricyclic antidepressant is injected dermally.

14. The method to claim 1 wherein the tricyclic antidepressant is applied topically.

15. The method to claim 1 wherein the tricyclic antidepressant is applied as a patch.

16. The method is claim 1 wherein the tricyclic antidepressant is administered by inhalation.

* * * * *